US009308378B2

(12) United States Patent
Shelton et al.

(10) Patent No.: US 9,308,378 B2
(45) Date of Patent: Apr. 12, 2016

(54) IMPLANT RECHARGER HANDSHAKING SYSTEM AND METHOD

(71) Applicant: ALFRED E. MANN FOUNDATION FOR SCIENTIFIC RESEARCH, Santa Clarita, CA (US)

(72) Inventors: Brian M. Shelton, Altadena, CA (US); Brian R. Dearden, Pasadena, CA (US); James H. Wolfe, Huntsville, AL (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 0 days.

(21) Appl. No.: 14/270,092

(22) Filed: May 5, 2014

(65) Prior Publication Data

US 2014/0330348 A1    Nov. 6, 2014

Related U.S. Application Data

(60) Provisional application No. 61/819,453, filed on May 3, 2013.

(51) Int. Cl.
*A61N 1/37* (2006.01)
*A61N 1/372* (2006.01)
*A61N 1/378* (2006.01)

(52) U.S. Cl.
CPC .......... *A61N 1/37217* (2013.01); *A61N 1/3787* (2013.01)

(58) Field of Classification Search
None
See application file for complete search history.

(56) References Cited

U.S. PATENT DOCUMENTS

| 3,646,940 A | 3/1972 | Timm et al. |
| 3,942,535 A | 3/1976 | Schulman et al. |
| 4,019,518 A | 4/1977 | Maurer et al. |
| 4,044,774 A | 8/1977 | Corbin et al. |
| 4,082,097 A | 4/1978 | Mann et al. |
| 4,340,062 A | 7/1982 | Thompson et al. |

(Continued)

FOREIGN PATENT DOCUMENTS

| DE | 102010006837 A1 | 8/2011 |
| EP | 1680182 | 7/2006 |

(Continued)

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994, pp. 148-152.

(Continued)

*Primary Examiner* — Brian T Gedeon
*Assistant Examiner* — Ankit Tejani
(74) *Attorney, Agent, or Firm* — Kilpatrick Townsend & Stockton LLP

(57) ABSTRACT

Systems, methods, and devices for wireless recharging of an implanted device. In response to receiving identification information from an implanted device, a charger can set an electrical field to a first field strength and receive first field strength information from the implanted device. The charger can then set the electrical field to a second field strength and receive second field strength information from the implanted device. This information relating to the first and second field strengths can be used to determine whether to recharge the implanted device.

11 Claims, 7 Drawing Sheets

(56) References Cited

U.S. PATENT DOCUMENTS

| | | |
|---|---|---|
| 4,468,723 A | 8/1984 | Hughes |
| 4,558,702 A | 12/1985 | Barreras et al. |
| 4,673,867 A | 6/1987 | Davis |
| 4,744,371 A | 5/1988 | Harris |
| 5,143,089 A | 9/1992 | Alt |
| 5,690,693 A | 11/1997 | Wang et al. |
| 5,702,428 A | 12/1997 | Tippey et al. |
| 5,702,431 A | 12/1997 | Wang et al. |
| 5,735,887 A | 4/1998 | Barreras, Sr. et al. |
| 5,741,316 A | 4/1998 | Chen et al. |
| 5,876,423 A | 3/1999 | Braun |
| 5,877,472 A | 3/1999 | Campbell et al. |
| 6,027,456 A | 2/2000 | Feler et al. |
| 6,035,237 A | 3/2000 | Schulman et al. |
| 6,055,456 A | 4/2000 | Gerber |
| 6,057,513 A | 5/2000 | Ushikoshi et al. |
| 6,067,474 A | 5/2000 | Schulman et al. |
| 6,076,017 A | 6/2000 | Taylor et al. |
| 6,164,284 A | 12/2000 | Schulman et al. |
| 6,172,556 B1 | 1/2001 | Prentice |
| 6,178,353 B1 | 1/2001 | Griffith et al. |
| 6,185,452 B1 | 2/2001 | Schulman et al. |
| 6,191,365 B1 | 2/2001 | Avellanet |
| 6,208,894 B1 | 3/2001 | Schulman et al. |
| 6,212,431 B1 | 4/2001 | Hahn et al. |
| 6,221,513 B1 | 4/2001 | Lasater |
| 6,246,911 B1 | 6/2001 | Seligman |
| 6,249,703 B1 | 6/2001 | Stanton et al. |
| 6,265,789 B1 | 7/2001 | Honda et al. |
| 6,306,100 B1 | 10/2001 | Prass |
| 6,313,779 B1 | 11/2001 | Leung et al. |
| 6,315,721 B2 | 11/2001 | Schulman et al. |
| 6,354,991 B1 | 3/2002 | Gross et al. |
| 6,360,750 B1 | 3/2002 | Gerber et al. |
| 6,393,325 B1 | 5/2002 | Mann et al. |
| 6,427,086 B1 | 7/2002 | Fischell et al. |
| 6,438,423 B1 | 8/2002 | Rezai et al. |
| 6,442,434 B1 | 8/2002 | Zarinetchi et al. |
| 6,466,817 B1 | 10/2002 | Kaula et al. |
| 6,505,075 B1 | 1/2003 | Weiner |
| 6,516,227 B1 | 2/2003 | Meadows et al. |
| 6,521,350 B2 | 2/2003 | Fey et al. |
| 6,564,807 B1 | 5/2003 | Schulman et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,652,449 B1 | 11/2003 | Gross et al. |
| 6,662,051 B1 | 12/2003 | Eraker et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,864,755 B2 | 3/2005 | Moore |
| 6,892,098 B2 | 5/2005 | Ayal et al. |
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,986,453 B2 | 1/2006 | Jiang et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B2 | 5/2006 | Whitehurst et al. |
| 7,069,081 B2 | 6/2006 | Biggs et al. |
| 7,114,502 B2 | 10/2006 | Schulman et al. |
| 7,127,298 B1 | 10/2006 | He et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,245,972 B2 | 7/2007 | Davis |
| 7,286,880 B2 | 10/2007 | Olson et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,331,499 B2 | 2/2008 | Jiang et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,496,404 B2 | 2/2009 | Meadows et al. |
| 7,513,257 B2 | 4/2009 | Schulman et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |

(56) References Cited

U.S. PATENT DOCUMENTS

| | | |
|---|---|---|
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2002/0116042 A1 | 8/2002 | Boling |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2007/0073357 A1 | 3/2007 | Rooney et al. |
| 2007/0265675 A1 | 11/2007 | Lund et al. |
| 2007/0293914 A1 | 12/2007 | Woods et al. |
| 2008/0132961 A1 | 6/2008 | Jaax et al. |
| 2008/0172109 A1 | 7/2008 | Rahman et al. |
| 2008/0183236 A1 | 7/2008 | Gerber |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2010/0076254 A1 | 3/2010 | Jimenez et al. |
| 2010/0076534 A1 | 3/2010 | Mock |
| 2011/0152959 A1 | 6/2011 | Sherwood et al. |
| 2011/0270269 A1 | 11/2011 | Swoyer et al. |
| 2011/0278948 A1 | 11/2011 | Forsell |
| 2011/0282416 A1 | 11/2011 | Hamann et al. |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2012/0276854 A1 | 11/2012 | Joshi et al. |
| 2012/0276856 A1 | 11/2012 | Joshi et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0023958 A1 | 1/2013 | Fell |
| 2013/0310894 A1 | 1/2013 | Allen et al. |
| 2013/0096651 A1 | 4/2013 | Ozawa |
| 2013/0150925 A1 | 6/2013 | Vamos et al. |
| 2013/0197608 A1 | 8/2013 | Eiger |
| 2013/0207863 A1 | 8/2013 | Joshi |
| 2013/0211479 A1 | 8/2013 | Olson et al. |
| 2013/0303942 A1 | 11/2013 | Damaser et al. |
| 2013/0331909 A1 | 12/2013 | Gerber |
| 2014/0222112 A1 | 8/2014 | Fell |
| 2014/0237806 A1 | 8/2014 | Smith et al. |
| 2015/0214604 A1 | 7/2015 | Zhao et al. |

FOREIGN PATENT DOCUMENTS

| | | |
|---|---|---|
| EP | 1904153 | 4/2008 |
| EP | 2243509 | 10/2010 |
| JP | 2003047179 A | 2/2003 |
| WO | WO 00-56677 A1 | 3/2000 |
| WO | WO 00-66221 A1 | 11/2000 |
| WO | WO 02/003408 A2 | 1/2002 |
| WO | WO 2004-103465 A1 | 12/2004 |
| WO | WO 2007090243 A1 * | 8/2007 |
| WO | WO 2008/021524 | 2/2008 |
| WO | WO 2009-051539 A1 | 4/2009 |
| WO | WO 2009-091267 A2 | 7/2009 |
| WO | WO 2010-042056 A1 | 4/2010 |
| WO | WO 2010-042057 A1 | 4/2010 |
| WO | WO 2011/059565 | 5/2011 |
| WO | WO 2013/141884 | 9/2013 |

OTHER PUBLICATIONS

Gundason, G., "A low-power ASK demodulator for Inductively coupled implantable electronics", Solid-State Circuits Conference, 2000, Esscirc "00, Proceedings of the 26rd European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, pp. 763-771.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circitis and Systems, 2006, APCCAS 2006, IEEE Asia Pacific Conference on IEEE, Piscataway, NJ, USA, Dec. 1, 2006, pp. 696-699.

(56) References Cited

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.

Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.

Tanagho, E., et al., Bladder Pacemaker: Scientific Basis and Clinical Future, Urology, Dec. 1982, vol. 20, No. 6, pp. 614-619.

\* cited by examiner

IMPLANT RECHARGER HANDSHAKING SYSTEM AND METHOD

CROSS-REFERENCES TO RELATED APPLICATIONS

This application claims the benefit of U.S. Provisional Application No. 61/819,453, entitled "IMPLANT RECHARGER HANDSHAKING MECHANISM," and filed on May 3, 2013, the entirety of which is hereby incorporated by reference herein.

BACKGROUND

The prevalence of use of medical devices in treating ailments is increasing with time. In many instances, and as these medical devices are made smaller, these medical devices are frequently implanted within a patient. To the extent that these devices use an implanted power source to power themselves, the recharging of the implanted power source can be a frequent and tedious task.

In many instances, device and tissue heating can be a significant concern with rechargeable, implantable medical devices. These heating concerns particularly arise during recharging. Specifically if the charge field is too weak, the implantable medical device will not quickly recharge, however, if the charge field is too strong, the implantable medical device may overheat, thereby causing implantee discomfort, and potentially injuring the implantee. Accordingly, systems, methods, and devices are desired to improve recharging of implantable medical devices.

BRIEF SUMMARY

One aspect of the present disclosure relates to a method of charging an energy storage device of an implantable pulse generator using an external charger. The method includes wirelessly receiving at the external charger an identifier corresponding to the implantable pulse generator, wirelessly receiving at the external charger information from the implantable pulse generator corresponding to a first sensed electrical field strength, at the external charger, changing the strength of the electrical field, after changing the strength of the electrical field, wirelessly receiving at the external charger information from the implantable pulse generator corresponding to a second sensed electrical field strength, and in response to the received information corresponding to the first and second sensed electrical fields, charging the energy storage device of the implantable pulse generator using the external charger.

In some embodiments, the method includes setting a first strength of the electrical field at the external charger, and in some embodiments, the first strength of the electrical field set at the external charger is zero, while in other embodiments, the first strength of the electrical field set at the external charger is non-zero. In some embodiments, charging the energy storage device of the implantable pulse generator further includes changing the strength of the electrical field to a third strength at the external charger. In some embodiments, the method includes determining the third strength of the electrical field, which third strength of the electrical field can be, for example, determined based on at least one of: a parameter of the implantable pulse generator, the external charger information corresponding to a first sensed electrical field strength, and the external charger information corresponding to the second sensed electrical field strength.

In some embodiments of the method, the parameter of the implantable pulse generator identifies one of: a charge state of the energy storage device, a temperature, a shunt current, and a maximum charge rate of the energy storage device. In some embodiments, the method includes terminating charging when a desired charge state is achieved. In some embodiments, the desired charge state is determined from one of a temperature and a shunt current.

One aspect of the present disclosure relates to a wireless charging system. The wireless charging system includes an implantable pulse generator. The implantable pulse generator can include an energy storage device. In some embodiments, the implantable pulse generator can transmit information concerning: (i) a first sensed electrical field strength at a first time, and (ii) a second sensed electrical field strength at a second time. In some embodiments, the system can include an external charger that can receive the transmitted information from the implantable pulse generator and initiate charging of the energy storage device when the transmitted information about the first and second sensed electrical field strength corresponds to information about the state of an electrical field generated by the external charger at the first and second times.

In some embodiments, the external charger can vary the strength of the electrical field based on information received from the implantable pulse generator. In some embodiments, the information received from the implantable pulse generator identifies one of a charge state, a shunt current, and a temperature. In some embodiments, the external charger can change the state of the electrical field to a third strength during charging of the energy storage device. The external charger can, for example, determine the third strength of the electrical field based on at least one of: a parameter of the implantable pulse generator, the transmitted information concerning the first sensed electrical field strength at the first time, and the transmitted information concerning the second sensed electrical field strength at the second time.

In some embodiments of the system, the implantable pulse generator can transmit data relating to at least one of: temperature; and a charge state during the charging of the energy storage device. In some embodiments, the external charger can terminate charging when one of: a temperature threshold is exceeded, and a desired charge state is attained.

One aspect of the present disclosure relates to a method of charging an energy storage device of an implantable pulse generator using an external charger. The method can include wirelessly receiving at the external charger an identifier corresponding to a first implantable pulse generator, wirelessly receiving at the external charger information from the first implantable pulse generator corresponding to a first sensed electrical field strength, at the external charger, changing the strength of the electrical field, after changing the strength of the electrical field, wirelessly receiving at the external charger information from the first implantable pulse generator corresponding to a second sensed electrical field strength, and in response to the received information corresponding to the first and second sensed electrical fields, determining not to recharge the first implantable pulse generator.

In some embodiments, the method includes determining an inability to recharge the first implantable pulse generator based on the information corresponding to the first sensed electrical field. In one exemplary embodiment, the inability to recharge the first implantable pulse generator can be determined if the information corresponding to the first sensed electrical field indicates a source of the electrical field other than the external charger. The method can include, selecting a second implantable pulse generator based on a first sensed electrical field strength at the second implantable pulse generator and a second sensed electrical field strength at the second implantable pulse generator, and charging the second implantable pulse generator.

In some embodiment of the method, charging the second implantable pulse generator can include changing the strength of the electrical field so that the electrical field is detectable by the second implantable pulse generator and is not detectable by the first implantable pulse generator. In one exemplary embodiment, the method can include comparing the information corresponding to the second sensed electrical field to a threshold, and determining that the sensed electrical field is too weak to recharge the first implantable pulse generator. The method can include selecting a second implantable pulse generator based on a first sensed electrical field strength at the second implantable pulse generator and a second sensed electrical field strength at the second implantable pulse generator, and charging the second implantable pulse generator. In some embodiments, charging the second implantable pulse generator can include changing the strength of the electrical field so that the electrical field is detectable by the second implantable pulse generator and is not detectable by the first implantable pulse generator.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

Figure 1:
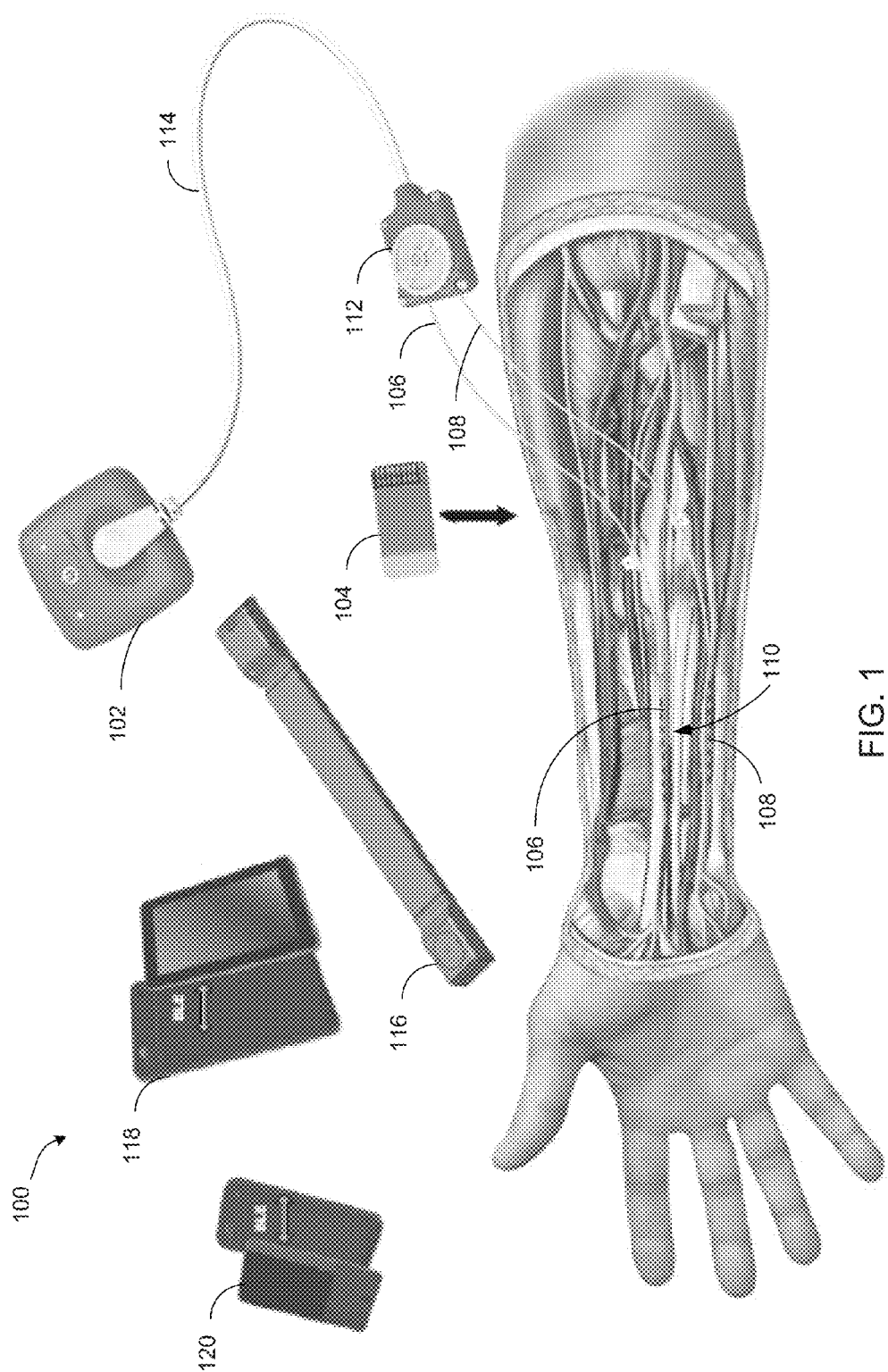
FIG. 1 is a schematic illustration of one embodiment of an implantable neurostimulation system.

In the appended figures, similar components and/or features may have the same reference label. Where the reference label is used in the specification, the description is applicable to any one of the similar components having the same reference label.

DETAILED DESCRIPTION OF THE INVENTION

A significant percentage of the Western (EU and US) population is affected by Neuropathic pain (chronic intractable pain due to nerve damage). In many people, this pain is severe. There are thousands of patients that have chronic intractable pain involving a nerve. Neuropathic pain can be very difficult to treat with only half of patients achieving partial relief. Thus, determining the best treatment for individual patients remains challenging. Conventional treatments include certain antidepressants, anti-epileptic drugs and opioids. However, side effects from these drugs can be detrimental. In some of these cases, electrical stimulation can provide effect treatment of this pain without the drug-related side effects.

A spinal cord stimulator is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. Early SCS trials were based the Gate Control Theory, which posits that pain is transmitted by two kinds of afferent nerve fibers. One is the larger myelinated Aδ fiber, which carries quick, intense-pain messages. The other is the smaller, unmyelinated "C" fiber, which transmits throbbing, chronic pain messages. A third type of nerve fiber, called Aβ, is "non-nociceptive," meaning it does not transmit pain stimuli. The gate control theory asserts that signals transmitted by the Aδ and C pain fibers can be thwarted by the activation/stimulation of the non-nociceptive Aβ fibers and thus inhibit an individual's perception of pain. Thus, neurostimulation provides pain relief by blocking the pain messages before they reach the brain.

SCS is often used in the treatment of failed back surgery syndrome, a chronic pain syndrome that has refractory pain due to ischemia. SCS complications have been reported in a large portion, possibly 30% to 40%, of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: including lead extension connection issues, lead breakage, lead migration and infection.

Peripheral neuropathy may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). As FDA approved PNS devices have not been commercially available in the US market, Standard spinal cord stimulator (SCS) devices are often used off label by pain physicians to treat this condition. A significant portion of SCS devices that have been sold may have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdominal or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates being far too high within the first few years of implantation. Many or even most complications result in replacement surgery and even multiple replacement surgeries in some cases.

One embodiment of an implantable neurostimulation system 100 is shown in FIG. 1, which implantable neurostimulation system 100 can be, for example, a peripherally-implantable neurostimulation system 10. In some embodiments, the implantable neurostimulation system 100 can be used in treating patients with, for example, chronic, severe, refractory neuropathic pain originating from peripheral nerves. In some embodiments, the implantable neurostimulation system 100 can be used to either stimulate a target peripheral nerve or the posterior epidural space of the spine.

The implantable neurostimulation system 100 can include one or several pulse generators. A person of skill in the art will recognize that although pulse generators are referred to herein as a recharged device, any implanted device can be recharged according to the systems and methods disclosed herein. The pulse generators can comprise a variety of shapes and sizes, and can be made from a variety of materials. In some embodiments, the one or several pulse generators can generate electrical pulses that are delivered to a nerve to control pain. One or both of the pulse generators can include a processor and/or memory. In some embodiments, the processor can provide instructions to and receive information from the other components of the implantable neurostimulation system 100. The processor can act according to stored instructions, which stored instructions can be located in memory, associated with the processor, and/or in other components of the content injection system 100. The processor can, in accordance with stored instructions, make decisions. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In some embodiments, the memory of one or both of the pulse generators can be the storage medium containing the stored instructions. The memory may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory may be implemented within the processor or external to the processor. In some embodiments, the memory can be any type of long term, short term, volatile, nonvolatile, or other storage medium and is not to be limited to any particular type of memory or number of memories, or type of media upon which memory is stored. In some embodiments, the memory can include, for example, one or both of volatile and nonvolatile memory. In one specific embodiment, the memory can include a volatile portion such as RAM memory, and a nonvolatile portion such as flash memory.

In some embodiments, one of the pulse generators can be an external pulse generator 102 or an implantable pulse generator 104. The external pulse generator 102 can be used to evaluate the suitability of a patient for treatment with the implantable neurostimulation system 100 and/or for implantation of an implantable pulse generator 104.

In some embodiments, one of the pulse generators can be the implantable pulse generator 104, which can be sized and shaped, and made of material to allow implantation of the implantable pulse generator 104 inside of a body. In some embodiments, the implantable pulse generator 104 can be sized and shaped so as to allow placement of the implantable pulse generator 104 at any desired location in a body, and in some embodiments, placed proximate to a peripheral nerve such that leads (discussed below) are not tunneled across joints and/or such that extension cables are not needed.

In some embodiments, the electrical pulses generated by the pulse generator can be delivered to one or several nerves 110 and/or to tissue proximate to one or several nerves 110 via one or several leads. The leads can include conductive portions, referred to as electrodes, and non-conductive portions. The leads can have a variety of shapes, can be in a variety of sizes, and can be made from a variety of materials, which size, shape, and materials can be dictated by the application or other factors.

In some embodiments, the leads can include an anodic lead 106 and/or a cathodic lead 108. In some embodiments, the anodic lead 106 and the cathodic lead 108 can be identical leads, but can receive pulses of different polarity from the pulse generator. Alternatively, in some embodiments, each lead can alternatingly include anodic and cathodic electrodes.

In some embodiments, the leads can connect directly to the pulse generator, and in some embodiments, the leads can be connected to the pulse generator via a connector 112 and a connector cable 114. The connector 112 can comprise any device that is able to electrically connect the leads to the connector cable 114. Likewise, the connector cable can be any device capable of transmitting distinct electrical pulses to the anodic lead 106 and the cathodic lead 108.

In some embodiments, the implantable neurostimulation system 100 can include a charger 116 that can be configured to recharge the implantable pulse generator 104 when the implantable pulse generator 104 is implanted within a body. The charger 116 can comprise a variety of shapes, sizes, and features, and can be made from a variety of materials. Like the pulse generators 102, 104, the charger 116 can include a processor and/or memory having similar characteristics to those discussed above. In some embodiments, the charger 116 can recharge the implantable pulse generator 104 via an inductive coupling.

In some embodiments, one or several properties of the electrical pulses can be controlled via a controller. In some embodiments, these properties can include, for example, the frequency, strength, pattern, duration, or other aspects of the timing and magnitude of the electrical pulses. In one embodiment, these properties can include, for example, a voltage, a current, or the like. In one embodiment, a first electrical pulse can have a first property and a second electrical pulse can have a second property. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 1, the implantable neurostimulation system 100 includes a controller that is a clinician programmer 118. The clinician programmer 118 can be used to create one or several pulse programs, plans, or patterns and/or to select one or several of the created pulse programs, plans, or patterns. In some embodiments, the clinician programmer 118 can be used to program the operation of the pulse generators including, for example, one or both of the external pulse generator 102 and the implantable pulse generator 104. The clinician programmer 118 can comprise a computing device that can wiredly and/or wirelessly communicate with the pulse generators. In some embodiments, the clinician programmer 118 can be further configured to receive information from the pulse generators indicative of the operation and/or effectiveness of the pulse generators and the leads.

In some embodiments, the controller of the implantable neurostimulation system 100 can include a patient remote 120. The patient remote 120 can comprise a computing device that can communicate with the pulse generators via a wired or wireless connection. The patient remote 120 can be used to program the pulse generator, and in some embodiments, the patient remote 120 can include one or several pulse generation programs, plans, or patterns created by the clinician programmer 118. In some embodiments, the patient remote 120 can be used to select one or several of the pre-existing pulse generation programs, plans, or patterns and to select, for example, the duration of the selected one of the one or several pulse generation programs, plans, or patterns.

Advantageously, the above outlined components of the implantable neurostimulation system 100 can be used to control and provide the generation of electrical pulses to mitigate patient pain.

Figure 2:
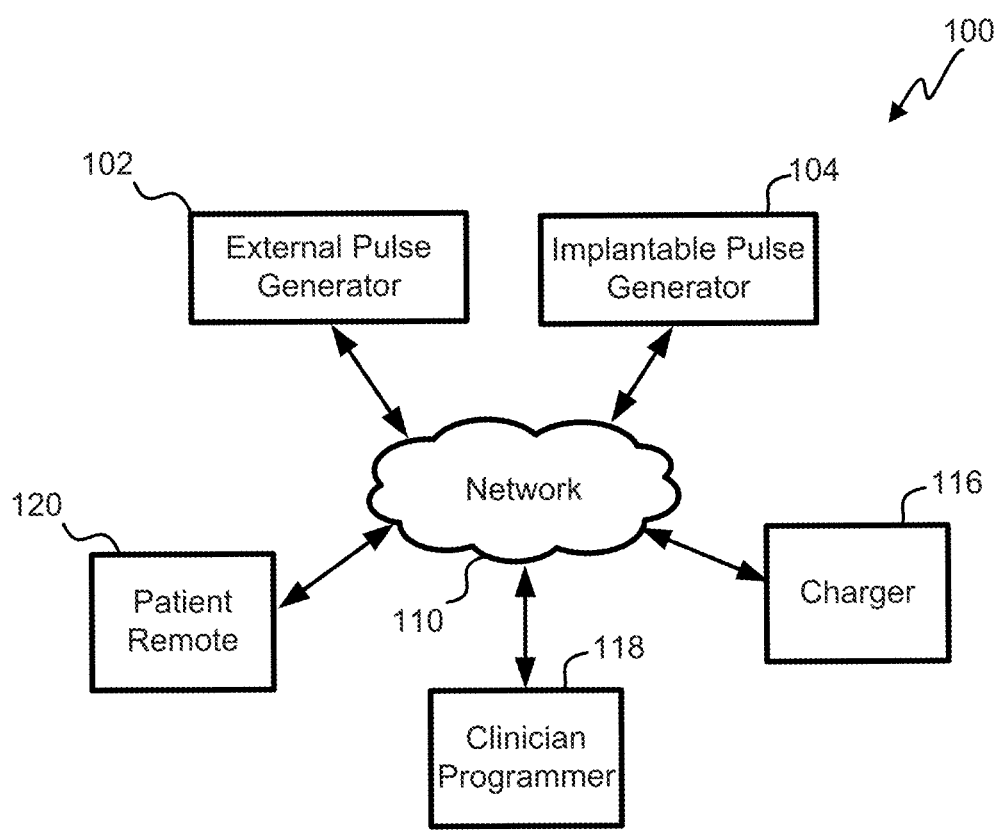
FIG. 2 is a schematic illustration of one embodiment of interconnectivity of the implantable neurostimulation system.

With reference now to FIG. 2, a schematic illustration of one embodiment of interconnectivity of the implantable neurostimulation system 100 is shown. As seen in FIG. 2, several of the components of the implantable neurostimulation system 100 are interconnected via network 110. In some embodiments, the network 110 allows communication between the components of the implantable neurostimulation system 100. The network 110 can be, for example, a local area network (LAN), a wide area network (WAN), a wired network, a custom network, wireless network, a telephone network such as, for example, a cellphone network, the Internet, the World Wide Web, or any other desired network or combinations of different networks. In some embodiments, the network 110 can use any desired communication and/or network protocols. The network 110 can include any communicative interconnection between two or more components of the implantable neurostimulation system 100. In one embodiment, the communications between the devices of the implantable neurostimulation system 100 can be according to any communication protocol including, for example those covered by Near Field Communication (NFC), Bluetooth, or the like. In some embodiments, different components of the system may utilize different communication networks and/or protocols.

Figure 3:
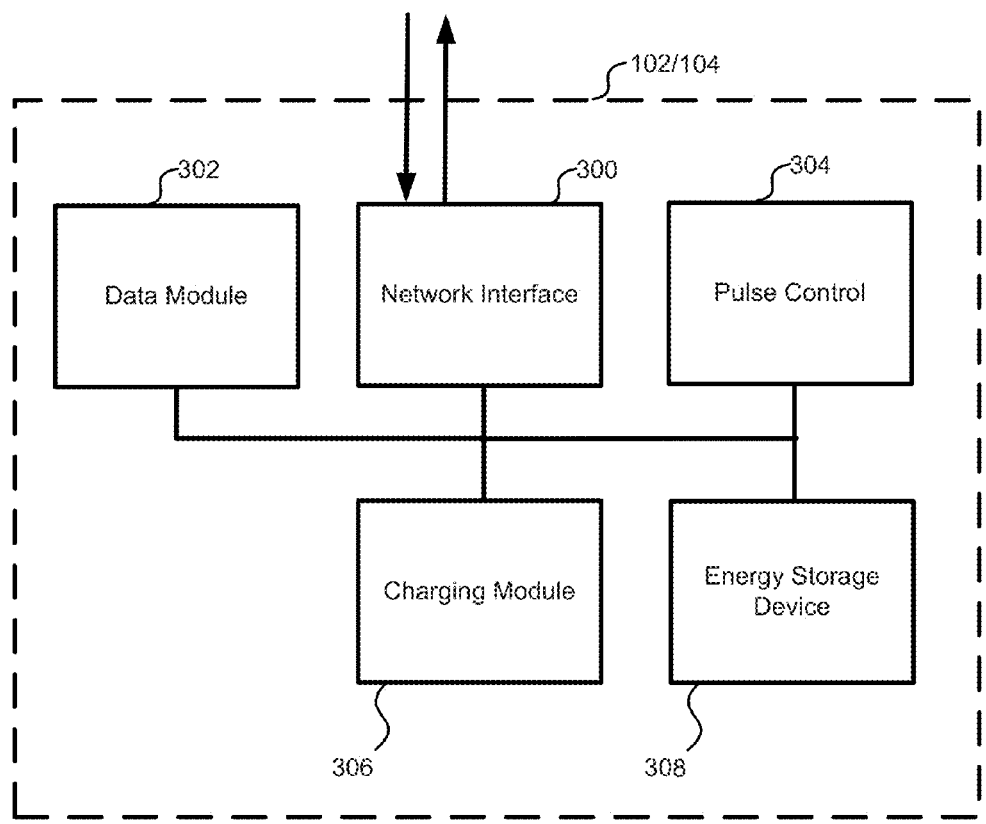
FIG. 3 is a schematic illustration of one embodiment of the architecture of the external pulse generator and/or of the implantable pulse generator that is a part of the implantable neurostimulation system.

With reference now to FIG. 3, a schematic illustration of one embodiment of the architecture of the external pulse generator 102 and/or of the implantable pulse generator 104 is shown. In some embodiments, each of the components of the architecture of the one of the pulse generators 102, 104 can be implemented using the processor, memory, and/or other hardware component of the one of the pulse generators 102, 104. In some embodiments, the components of the architecture of the one of the pulse generators 102, 104 can include software that interacts with the hardware of the one of the pulse generators 102, 104 to achieve a desired outcome.

In some embodiments, the pulse generator 102/104 can include, for example, a network interface 300. The network interface 300 can be configured to access the network 110 to allow communication between the pulse generator 102, 104 and the other components of the implantable neurostimulation system 100. In some embodiments, the network interface 300 can include one or several antennas and software configured to control the one or several antennas to send information to and receive information from one or several of the other components of the implantable neurostimulation system 100.

The pulse generator 102, 104 can further include a data module 302. The data module 302 can be configured to manage data relating to the identity and properties of the pulse generator 102, 104. In some embodiments, the data module can include one or several database that can, for example, include information relating to the pulse generator 102, 104 such as, for example, the identification of the pulse generator, one or several properties of the pulse generator 102, 104, or the like. In one embodiment, the data identifying the pulse generator 102, 104 can include, for example, a serial number of the pulse generator 102, 104 and/or other identifier of the pulse generator 102, 104 including, for example, a unique identifier of the pulse generator 102, 104. In some embodiments, the information associated with the property of the pulse generator 102, 104 can include, for example, data identifying the function of the pulse generator 102, 104, data identifying the power consumption of the pulse generator 102, 104, data identifying the charge capacity of the pulse generator 102, 104 and/or power storage capacity of the pulse generator 102, 104, data identifying potential and/or maximum rates of charging of the pulse generator 102, 104, and/or the like.

The pulse generator 102, 104 can include a pulse control 304. In some embodiments, the pulse control 304 can be configured to control the generation of one or several pulses by the pulse generator 102, 104. In some embodiments, for example, this information can identify one or several pulse patterns, programs, or the like. This information can further specify, for example, the frequency of pulses generated by the pulse generator 102, 104, the duration of pulses generated by the pulse generator 102, 104, the strength and/or magnitude of pulses generated by the pulse generator 102, 104, or any other details relating to the creation of one or several pulses by the pulse generator 102, 104. In some embodiments, this information can specify aspects of a pulse pattern and/or pulse program, such as, for example, the duration of the pulse pattern and/or pulse program, and/or the like. In some embodiments, information relating to and/or for controlling the pulse generation of the pulse generator 100 to 104 can be stored within the memory.

The pulse generator 102, 104 can include a charging module 306. In some embodiments, the charging module 306 can be configured to control and/or monitor the charging/recharging of the pulse generator 102, 104. In some embodiments, for example, the charging module 306 can include one or several features configured to receive energy for recharging the pulse generator 102, 104 such as, for example, one or several inductive coils/features that can interact with one or several inductive coils/features of the charger 116 to create an inductive coupling to thereby recharge the pulse generator 102, 104.

In some embodiments, the charging module 306 can include hardware and/or software configured to monitor the charging of the pulse generator 102, 104. In some embodiments, these features can be configured to monitor the temperature of one or several components of the pulse generator 102, 104, the rate of charge of the pulse generator 102, 104, the charge state of the pulse generator 102, 104, or the like. These features can include, for example, one or several resistors, thermistors, thermocouples, temperature sensors, current sensors, charge sensors, or the like.

The pulse generator 102, 104 can include an energy storage device 308. The energy storage device 308 can be any device configured to store energy and can include, for example, one or several batteries, capacitors, fuel cells, or the like. In some embodiments, the energy storage device 308 can be configured to receive charging energy from the charging module 306.

Figure 4:
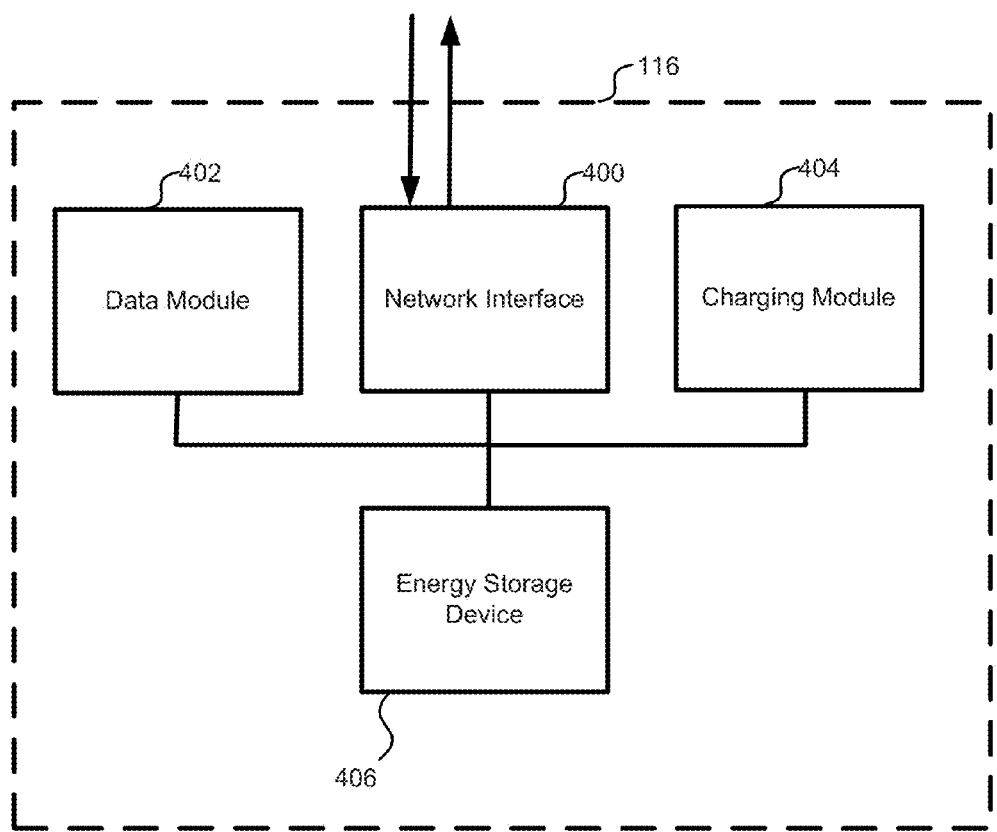
FIG. 4 is a schematic illustration of one embodiment of the charger that is a part of the implantable neurostimulation system.

With reference now to FIG. 4, a schematic illustration of one embodiment of the charger 116 is shown. In some embodiments, each of the components of the architecture of the charger 116 can be implemented using the processor, memory, and/or other hardware component of the charger 116. In some embodiments, the components of the architecture of the charger 116 can include software that interacts with the hardware of the charger 116 to achieve a desired outcome.

In some embodiments, the charger 116 can include, for example, a network interface 400. The network interface 400 can be configured to access the network 110 to allow communication between the charger 116 and the other components of the implantable neurostimulation system 100. In some embodiments, the network interface 400 can include one or several antennas and software configured to control the one or several antennas to send information to and receive information from one or several of the other components of the implantable neurostimulation system 100.

In some embodiments, the charger 116 can include a data module 402. The data module 402 can be configured to manage data relating to the identity and properties of the pulse generator 102, 104 with which the charger 116 is communicating. In some embodiments, the data module 402 can include one or several database that can include, for example, the identification of the one or several pulse generators 102, 104 with which the charger 116 is communicating, one or several properties of the one or several pulse generators 102, 104 with which the charger is communicating, or the like. This information can include some or all of the information discussed above with respect to the data module 302.

The charger 116 can include a charging module 404. The charging module 404 can be configured to control and/or monitor the charging of one or several of the pulse generators 102, 104. In some embodiments, for example, the charging module 404 can include one or several protocols that can request information from the one or several pulse generators 102, 104 at one or several times before, during, and after charging. This information can be received by the charger 116 from the pulse generator 102, 104 and can be used to control the generation of and/or properties of the charge field. In some embodiments, the charging module 404 can include one or several features configured to transmit energy for recharging the pulse generator 102, 104 such as, for example, one or several inductive coils/features that can interact with one or several inductive coils/features of the pulse generator 102, 104 to create an inductive coupling to thereby recharge the pulse generator 102, 104.

The charger 116 can include an energy storage device 406. The energy storage device 406 can be any device configured to store energy and can include, for example, one or several batteries, capacitors, fuel cells, or the like. In some embodiments, the energy storage device 406 can be configured to provide charging energy to the one or several pulse generators 102, 104 being recharged.

Figure 5:
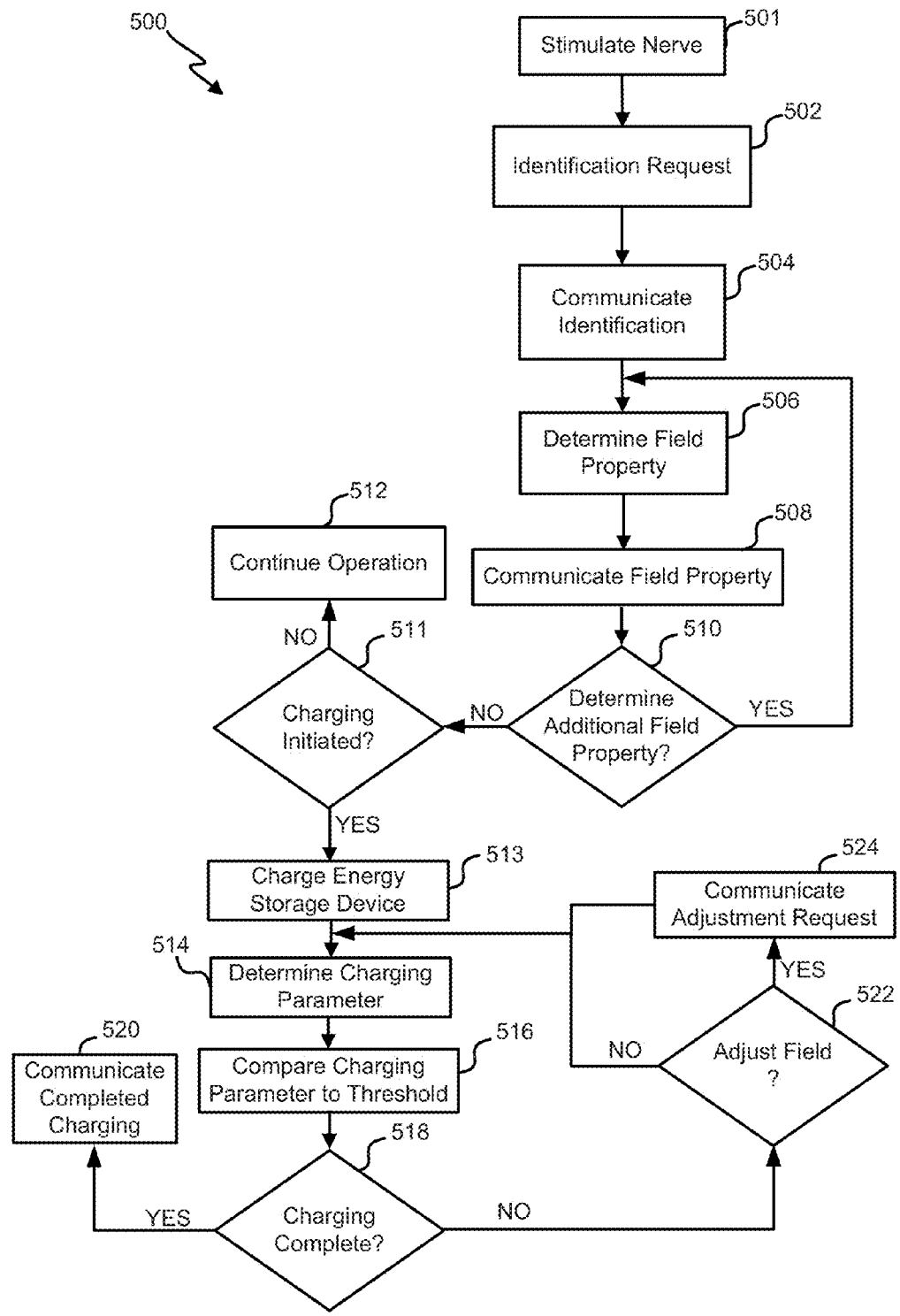
FIG. 5 is a flowchart illustrating one embodiment of a process for charging a pulse generator.

With reference now to FIG. 5, a flowchart illustrating one embodiment of a process 500 for charging a pulse generator 102, 104 is shown. The process 500 can be performed by and/or on a pulse generator 102, 104 that can be, for example, in communication with the charger 116. The process begins at block 501 wherein a nerve is stimulated. In some embodiments, the stimulation of the nerve can include the generation of one or several pulses according to one or several pulse programs. This can include retrieving information from, for example, the pulse control 304 of the pulse generator 102, 104, and generation of pulses according to the pulse program retrieved from the pulse control 304. In some embodiments, these pulses can be delivered to one or several targeted areas that can include, for example, one or several targeted nerves via electrodes 106, 108. In some embodiments, the stimulation of block 501 can be performed during the entire process 500, and in some embodiments, process 500 can be performed independent of the stimulation of block 501. Thus, in some embodiments, process 500 may be performed while stimulation occurs, when stimulation does not occur, or partially while stimulation occurs.

After the nerve has been stimulated, the process 500 proceeds to block 502 wherein an identification request is received. In some embodiments, the identification request can be received from the charger 116 via, for example, the network interface 300. In some embodiments, the identification request can be received as the first step in triggering and/or initiating the charging of the pulse generator 102, 104. In some embodiments, the identification request can include a request for information identifying the pulse generator 102, 104, which information can include, for example, the serial number of the pulse generator 102, 104.

After the identification request has been received, the process 500 proceeds to block 504 wherein the identification of the pulse generator 102, 104 is communicated. In some embodiments, this can include, for example, retrieving information identifying the pulse generator 102, 104 from the data module 302 of the pulse generator 102, 104. In some embodiments, this can further include the retrieval of information relating to one or several parameters of the pulse generator 102, 104 such as, for example, the charge state of the energy storage device 308 of the pulse generator 102, 104, one or several charging parameters of the pulse generator 102, 104 such as, for example, the rates with which the pulse generator 102, 104 can be charged, and/or the like. In some embodiments, the retrieved information can be combined into a message which can be communicated from the pulse generator 102, 104 to the charger 116 via the of the network interface 300 of the pulse generator 102, 104.

The communication of the identification of the pulse generator 102, 104 can be performed in response to the receipt of the identification request in block 502, and in some embodiments, the communication of the identification of the pulse generator 102, 104 can be periodically performed without the receipt of the identification request of block 502. In some embodiments, the communication of the identification can be triggered in response to the charge state of the energy storage device 308 of the pulse generator 102, 104 including, for example, when the charge state of the pulse generator 102, 104 drops below a threshold value.

After the identification has been communicated, the process 500 proceeds to block 506 wherein a field property is determined. In some embodiments, the field property can be a property of a charging field and/or of an electric field detectable at the pulse generator 102, 104. In some embodiments, the determination of the field property can include an identification of the strength of the electric field and/or of the charge field at one or several time points during the charging process. In some embodiments, the field property can be determined through the use of components of the charging module 306 such as, for example, one or several inductive coils, resistors, temperature sensors, or the like. In some embodiments, the field property may be determined in response to an instruction or a request from charger 116 or may be determined in response to a different trigger or in a predetermined manner.

After the field property has been identified, the process 500 proceeds to block 508 wherein the field property is communicated. In some embodiments, field property can be communicated to the charger 116 via the network interface 300 of the pulse generator 102, 104. In some embodiments, the communication of the field property can include the generation of a message containing the field property and the sending of the generated message to the charger 116.

After the field property has been communicated, the process 500 proceeds to decision state 510, wherein it is decided if an additional field property should be determined. In some embodiments, for example, the pulse generator 102, 104 can receive a request from the charger 116 to take the second and/or other additional field property at one or several other times during the charging process. Similarly, in some embodiments, the pulse generator 102, 104 can be configured to detect a second field property and/or multiple other field properties at one or several time periods during the charging process. Advantageously, the determination of one or several additional field properties at one or several additional times during the recharging can allow verification and/or identification of the ability of the charger 116 to manipulate and/or change the charge field detected by the pulse generator 102, 104. This can allow for better control during the recharging process.

If it is decided that an additional field property should be determined, whether via a request from the charger 116 and/or according to a protocol of the pulse generator 102, 104, the process 500 returns to block 506 and proceeds as outlined above. If it is decided that an additional field property should not be determined, then the process 500 proceeds to decision state 511, wherein it is determined if charging is initiated. In some embodiments, the determination of the initiation of charging can include receiving an instruction to begin charging. In some embodiments, this instruction can be received from, for example, the charger 116. In some embodiments, the determination of the initiation of charging can include detecting a property of the charging field enabling charging, such as, for example, a strength of the charging field that is greater than a threshold value, that is sufficiently large to allow charging, or the like. If it is determined that charging is not initiated, then the process proceeds to block 512 and continues operation. In some embodiments, the continued operation can include the continuing of the nerve stimulation identified in block 501, operating according to one or several pulse programs, plans, or patterns, operating according to one or several new instructions received from, for example, the clinician programmer 118 and/or the patient remote 120, or the like.

Returning again to decision state 511, if it is determined that charging has been initiated, then the process 500 proceeds to block 513, wherein the energy storage device 308 is charged. In some embodiments, the energy storage device 308 can be charged by energy received from the electric field via the charging module 306.

In some embodiments, while the energy storage device 308 is being charged, the process 500 determines and/or monitors one or several charging parameters of the energy storage device 308. In some embodiments, this monitoring can occur throughout the charging of the pulse generator 102, 104 and the monitoring can occur, for example, once, multiply, periodically, and/or continuously. In some embodiments, these parameters can include, for example, temperature of the energy storage device 308, temperature of one or several components of the pulse generator 102, 104, a rate of charge of the energy storage device 308, a charge state of the energy storage device 308, charge voltage, strength of charge field, amount of excess charge current, and/or the like.

After the parameter of the charging has been determined, the process 500 proceeds to block 516 wherein the charging parameter is compared to a threshold value. In some embodiments, this comparison of the charging parameter to the threshold value can be used to determine whether to adjust a property of the field, whether to change the rate of charging of the energy storage device 308, whether to stop the charging of the energy storage device 308, and/or the like. In some embodiments, for example, the threshold can be a temperature threshold, wherein a temperature above the threshold value is indicative of and/or can trigger a request to decrease the strength of the charge field, a rate of charge threshold, wherein the rated charge threshold is specified by some portion of the maximal and/or maximum charge rate of the pulse generator 102, 104, a charge state threshold, wherein the charge state threshold indicates the charge state of the energy storage device 308 of the pulse generator 102, 104, a charge voltage threshold, a strength of charge field threshold, an amount of excess charge current threshold, or the like.

After the charging parameter has been compared to a threshold, the process 500 proceeds to decision state 518 wherein it is determined if the charging is complete. In some embodiments, for example, the completeness of the charging can be determined based on the comparison of the charging parameter to one of the thresholds such as, for example, a temperature threshold, a charge state threshold, or the like.

If it is determined that the charging is complete, then the process 500 proceeds to block 520 wherein the completed charging is communicated. In some embodiments, the communication to complete a charging can include the generation of a message including information identifying the completed state of the charging by a processor of the pulse generator 102, 104, and/or indicating the charge state of the energy storage device 308 of the pulse generator 102, 104. Thus, in some embodiments, the communication can comprise a command to stop charging and/or a request to stop charging, and in some embodiments, the communication can comprise information that can be used by the charger 116 to determine whether to stop charging of the pulse generator 102, 104. In embodiments in which the communication comprises data that can be used by the charger 116 to determine whether to stop charging of the pulse generator 102, 104, the process 600 can generate the communication directly after determining the charging parameter in block 514. The communication can be sent from a pulse generator to the charger 116 via, for example, the network interface 300 of the pulse generator 102, 104.

Returning again to decision state 518, if it is determined that charging is not complete, then the process 500 proceeds to decision state 522 wherein it is determined if an adjustment of the charge field is desired and/or indicated. In some embodiments, this can include, determining if the result of the comparison of a charging parameter to one of the thresholds indicates that the charging field and/or the strength of the charging field should be either increased or decreased. In one embodiment, for example, the comparison of a charging parameter relating to the rate of charge of the pulse generator 102, 104 may indicate a rate of charge that is lower than a rate of charge threshold. In one such embodiment, the pulse generator 102, 104 may request an increase in the strength of the charging field. Similarly, in one embodiment, the comparison of a rate of charge charging parameter relating to the rate of charge with the threshold for the rated charge may indicate that the charging rate of the pulse generator 102, 104 is exceeding a threshold value In one such embodiments, it may be determined that the strength of the charging field should be decreased. Similarly, in some embodiments, a temperature exceeding a threshold value may be an indicator of a need to decrease the charging field, a comparison of a charging parameter indicating the charge state with the charge state threshold may indicate the need to decrease the strength of the charging field, or the like. If it is determined that the charging field does not need to be adjusted, then the process returns to block 514 and continues as outlined above.

If it is determined that the charging field should be adjusted, then the process 500 proceeds to block 524 wherein an adjustment request is communicated. In some embodiments, the communication adjustment request can include the creation of a message requesting the adjustment of the strength of the charging field, and in some embodiments, the message can comprise data, including one or several charging parameters determined in block 514 that can be used by the charger 116 to determine whether and how to adjust the charge field.

In some embodiments, the charging message may simply indicate whether to increment or decrement the strength of the charging field, and in some embodiments, the adjustment message may indicate a degree to which the strength of the charging field should be increased or decreased. In embodiments in which the message comprises data, including one or several charging parameters determined in block 514 that can be used by the charger 116 to determine whether and how to adjust the charge field, the process 600 can generate the message directly after determining the charging parameters in block 514. In some embodiments, the adjustment request can be communicated to the charger 116 from the pulse generator 102, 104 via the network interface 300. After the adjustment request has been communicated, or returning again to decision state 522, if it is determined that the charging field should not be adjusted, the process 500 returns to block 514 and continues as outlined above.

In one exemplary embodiment, the process 500 can be implemented as follows, the pulse generator 102, 104 can generate one or several pulses to stimulate a nerve and/or portion of the patient's body. While generating the one or several pulses, the pulse generator 102, 104 can receive an identification request and/or a charging request. In some embodiments, the pulse generator 102, 104 can retrieve information relating to the charge state of the energy storage device 308, and determine whether charging is desired and/or advisable. If charging is desired and/or advisable, the pulse generator 102, 104 can retrieve identification information from, for example, the data module 302 of the pulse generator 102, 104. This information can identify the pulse generator 102, 104.

After the pulse generator 102, 104 has received the identification request, the pulse generator 102, 104 can generate a message including information identifying the pulse generator 102, 104 and, in some embodiments, also including information relating to the pulse generator 102, 104. In some embodiments, this information relating to the pulse generator 102, 104 can include information relating to the charge state of the energy storage device 308, to acceptable rates of charge of the pulse generator 102, 104, and/or the like. This information relating to the pulse generator 102, 104 and identifying the pulse generator 102, 104 can be communicated to the charger 116 via, for example, the network interface 300.

After the identification information has been communicated to the charger 116, the pulse generator 102, 104 can, according to one or several protocols stored on pulse generator 102, 104, or according to a request received from the charger 116, determine a field property at a first time. In some embodiments, the field property can include a strength of a charge field which can, for example, be at a first level that can be, for example, zero and/or close to zero. In some embodiments, a zero charge field can comprise a field having a strength of less than 1 percent of the maximum charge strength, less than 5 percent of the maximum charge strength, less than 10 percent of the maximum charge strength, and/or any other or intermediate value. After the field property has been determined, the pulse generator 102, 104 can communicate the field property to the charger 116.

In some embodiments, after communicating the field property to the charger, the pulse generator 102, 104 can determine a second field property at a second time. In some embodiments, the second field property can be determined in response to request received from the charger 116 requesting information relating to a second field property at the second time, and in some embodiments, the second field property can be determined at the second time according to one or several protocols of the pulse generator 102, 104.

In some embodiments, after the second field property has been determined at the second time, the pulse generator 102, 104 can communicate the field property to the charger 116, and a signal initiating charging can be received and/or charging can be initiated. In some embodiments, one or several properties of the charge field and/or of the pulse generator 102, 104 can be monitored during the charging, and these properties can be compared to one or several thresholds to determine when to terminate charging, and/or whether to adjust the strength of the charge field. If it is determined to terminate charging, then a message indicating the completion of the charging is generated and sent. Similarly, if it is decided to adjust the strength of the charge field, then a message requesting an adjustment of the strength of the charge field is generated and sent.

Figure 6:
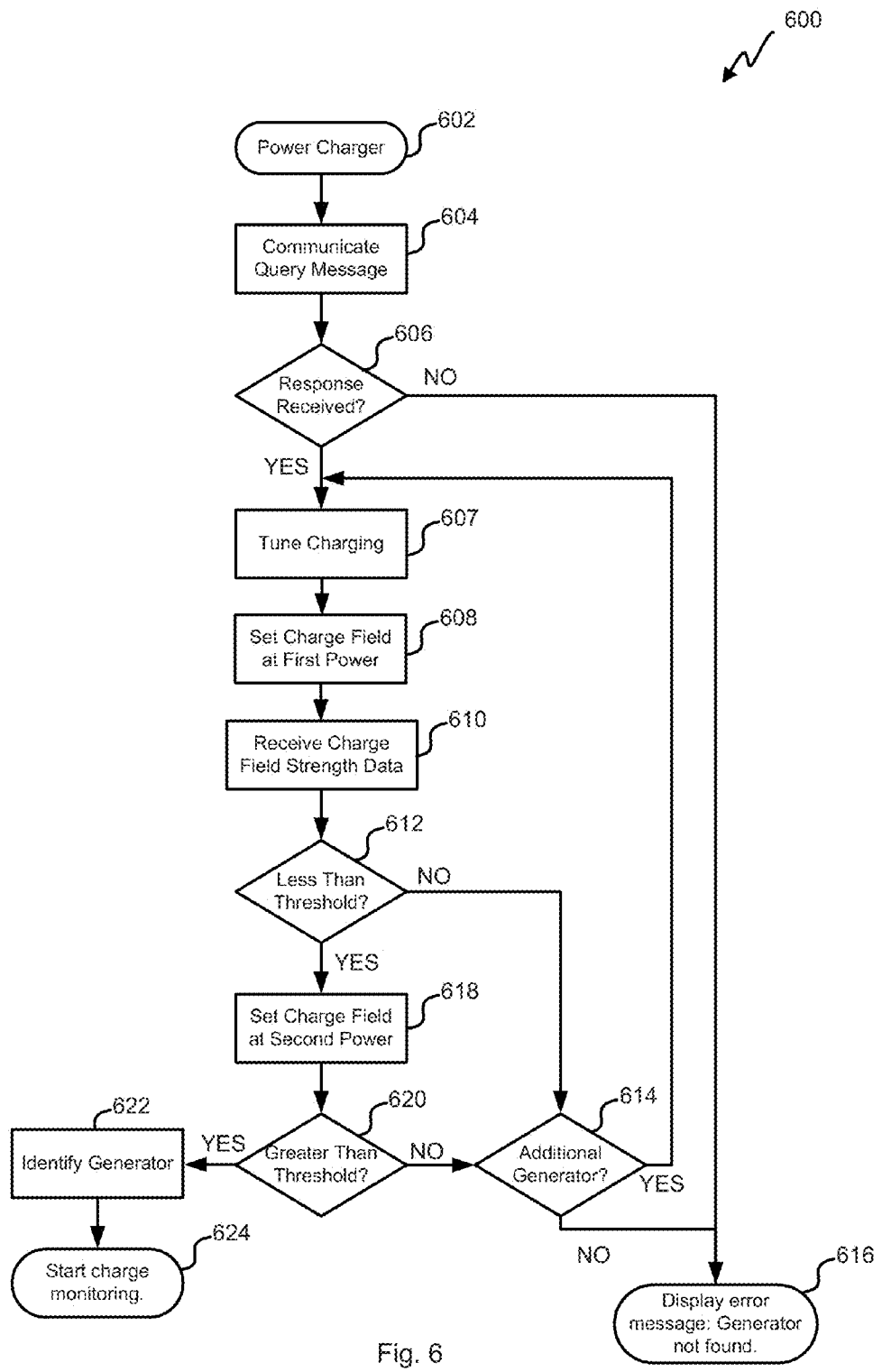
FIG. 6 is a flowchart illustrating one embodiment of a process for controlling charging of the pulse generator.

With reference now to FIG. 6, a flowchart illustrating one embodiment of a process 600 for controlling charging of the pulse generator 102, 104 is shown. The process 600 can be performed by and/or on charger 116. In some embodiments, the charger 116 can be, for example, in communication with the pulse generator 102, 104. The process 600 can begin a block 602, wherein the charger 116 is powered. In some embodiments, the powering of the charger 116 can occur when the charger 116 is turned on.

After the charger 116 is powered, the process 600 proceeds to block 604, wherein a query message is communicated. In some embodiments, the query message can comprise the identification request, and can include a request for identification of any pulse generators 102, 104 receiving the query message. In some embodiments, the query message can be generated by the charger 116 and can be communicated to one or several pulse generators 102, 104 via the network interface 400.

After the query message has been communicated, the process 600 proceeds to decision state 606, wherein it is determined if a response to the query message has been received. In some embodiments, the response can be the identification communication from block 504 of FIG. 5. In some embodiments, this determination can be made after a period such as, for example, 0.5 seconds, 1 second, 2 seconds, 5 seconds, and/or any other or intermediate length of time. If it is determined that no response has been received, then the process 600 proceeds to block 616 wherein an error is triggered and an error message is provided to the user. In some embodiments, the error message can indicate that no pulse generator 102, 104 was found, and the error message can be displayed to the user.

Returning again to decision state 606, if it is determined that a response was received, then the process 600 proceeds to block 607 wherein the charging frequency of the charger 116 is tuned by actively adjusting the tuning frequency of the charger 116, and specifically of the features of the charging module 404. In some embodiments, this tuning can result in the components of the charging module 404 operating at a frequency substantially equal to the resonant frequency of, for example, the features of the charging module 306 of the pulse generators 102, 104. This tuning can include measuring the output power of the charging module 404 and reporting the output power to the processor of the charger 116. The actual power delivered to the charging module 306 of the pulse generator 102, 104 can be measured and reported to the charger 116. Based on the actual power delivered to the charging module 306 of the pulse generator 102, 104 and the output power of the charging module 404 of the charger 116, the charger 116 may adjust the tuning frequency of the charging module 404 if the actual power delivered to the receiving coil is not at a desired level. This may be repeated until the charger determines that the actual power delivered to the charging module 306 of the pulse generator is at a desired level. In some embodiments, the tuning of block 607 can be performed before charging starts, at instance during charging, and/or continuously during charging. In some embodiments, the tuning of block 607 may be omitted from process 600.

The process 600 proceeds to block 608, wherein the charge field is set to first power and/or strength. In some embodiments, the charge field can be sent to a low first power and/or strength. In some embodiments, the low first power and/or strength can be used to identify whether one or several other charge fields can affect the charging of the pulse generator 102, 104. In some embodiments, the low first power can comprise a power that is 0% of the maximum charge field strength and/or power, 1% of the maximum charge field strength and/or power, 2% of the maximum charge field strength and/or power, 5% of the maximum charge field strength and/or power, 10% of the maximum charge field strength and/or power, 20% of the maximum charge field strength and/or power, and/or any other or intermediate percent of the maximum charge field strength and/or power.

After the charge field has been set to the first strength and/or power, the process 600 proceeds to block 610 wherein charge field strength data is received. In some embodiments, the charge field strength data can identify the strength of the charge field at the pulse generator 102, 104. In some embodiments, the charge field strength can be detected with components of the pulse generator 102, 104 including, for example, components of the charging module 306. The charge field strength data can be received at the charger 116 via the network interface 400 of the charger 116.

After the charge field strength data has been received, the process 600 proceeds to decision state 612 wherein it is determined if the charge field strength data indicates a detected charge field that is less than a threshold. In some embodiments, this comparison can identify whether electric fields from sources other than the charger 116 are detectable by the pulse generator 102, 104. In some embodiments, this comparison of the detected charge field strength to the charge field threshold can also provide an indication as to the degree to which the charger 116 can control the charging of the pulse generator 102, 104 or to which the pulse generator 102, 104 is within charging range of the charger 116. In some embodiments, the threshold can identify a value corresponding to a detected charge strength that can be, for example, greater than 50% of the first charge field power level, greater than 75% of the first charge field power level, greater than 90% of the first charge field power level, greater than 100% of the first charge field power level, greater than 110% of the first charge field power level, greater than 120% of the first charge field power level, greater than 150% of the first charge field power level, greater than 150% first charge field power level, greater than 200% of the first charge field power level, greater than 500% of the first charge field power level, greater than 1000% of the first charge field power level, greater than 10,000% of the first charge field power level, and/or any other or intermediate percent of the first charge field power level. If it is determined that the detected strength of the charge field is greater than the threshold, then the process proceeds to decision state 614 wherein it is determined if there is an additional pulse generator 102, 104. In some embodiments, this determination can include determining whether more than one response was received following the query message. If it is determined that there is an additional pulse generator 102, 104, then the process 600 returns to block 608 and proceeds as outlined above. If it is determined that there is no additional pulse generator 102, 104, then the process 600 proceeds to block 616 wherein an error is triggered and an error message is provided to the user. In some embodiments, the error message can indicate that no pulse generator 102, 104 was found, and the error message can be displayed to the user.

Returning again to decision state 612, if it is determined that the detected charge field strength and/or power is less than the threshold, then the process 600 proceeds to block 618 wherein the charge field is set to a second charge power. In some embodiments, setting the charge field to a second charge power and/or strength can include changing the strength of the charge power from a first non-zero strength to a second, increased strength, which strength can be, for example, the maximum charge field strength, and in some embodiments, can include changing the strength from a first zero strength to a second, increased strength, which strength can be, for example, the maximum charge field strength. In some embodiments, the charge field can be set to a high second charge power such as, for example, 75% of the maximum strength of the charge field power, 80% of the maximum strength the charge field power, 90% of the maximum strength of the charge field power, 100% of the maximum strength of the charge field power, and the/or any other intermediate percent of the maximum charge field value. Advantageously, setting the charge field at a second charge strength and/or power can be used to determine the proximity of the pulse generator 102, 104 to the charger 116.

In some embodiments, setting the charge field to a second power can further include receiving charge field strength data identifying a detected power of the charge field after the charge field has been set to the second charge field power.

After the charge field presence is set to the second power, the process 600 proceeds to decision state 620 wherein it is determined if the power and/or strength of the charge field as detected by the pulse generator 102, 104 is greater than a threshold. In some embodiments, this comparison can indicate if an adequate amount of the electrical field is detectable at the pulse generator 102, 104 to allow charging of the pulse generator 102, 104 at a desired rate. In some embodiments, the threshold can identify a percentage of the second charge field power level such as, for example, 60% of the second charge field power level, 70% of the second charge field power level, 70% of the second charge field power level, 80% of the second charge field power level, 90% of the second charge field power level, 100% of the second charge field power level, 110% of the second charge field power level, 120% of the second charge field power level, 150% of the second charge field power level, and/or any other or intermediate percent of the second charge field power level. In some embodiments, the comparison of the detected strength of the charge field to the second charge field power level via comparison to the threshold can include normalizing of the detected strength of the charge field based on the strength of the charge field detected in block 610. In some embodiments, this normalization can minimize any data skew that may be caused by electric fields from sources other than the charger 116. If it is determined that the detected strength of the charge field is less than the threshold, then the process 600 proceeds to decision state 614 and proceeds as outlined above.

If it is determined that the detected strength of the charge field is greater than the threshold, then the process 600 proceeds to block 622 and the pulse generator 102, 104 is identified. In some embodiments, this can include storing identification information of the identified pulse generator 102, 104 such as, for example, storing the serial number of the identified pulse generator.

After pulse generator 102, 104 has been identified, the process 600 proceeds to block 624 wherein charge monitoring is started. In some embodiments, the starting of charge monitoring can include the initiation of charging of the pulse generator 102, 104. In some embodiments, initiation of charging of the pulse generator 102, 104 can include setting the charge field to a third charge field strength. In some embodiments, this third charge field strength can be identified based on information associated with the pulse generator 102, 104 including, for example, the energy storage capacity of the energy storage device 308, the charge state of the energy storage device 308, the maximum rate of charge of the pulse generator 102, 104, one or several field properties determined by the pulse generator 102, 104 including, for example, the strength of the charge field at the first time and/or the strength of the charge field at the second time, and/or the like. In some embodiments, this information can be received from the pulse generator 102, 104 as part of block 504 of process 500, and in some embodiments, this information can be retrieved from the data module 402 of the charger 116. In some embodiments in which a plurality of pulse generators 102, 104 have been detected, the third charge field strength can be set to be detectable by one or several of the plurality of pulse generators 102, 104 and to be undetectable by one or several of the plurality of pulse generators 102, 104. After the third charge field strength has been identified, in some embodiments, the charger 116 can generate and send a message to the pulse generator 102, 104 indicating the initiation of charging. Further details of charge monitoring will be discussed with respect to FIG. 7 below.

Figure 7:
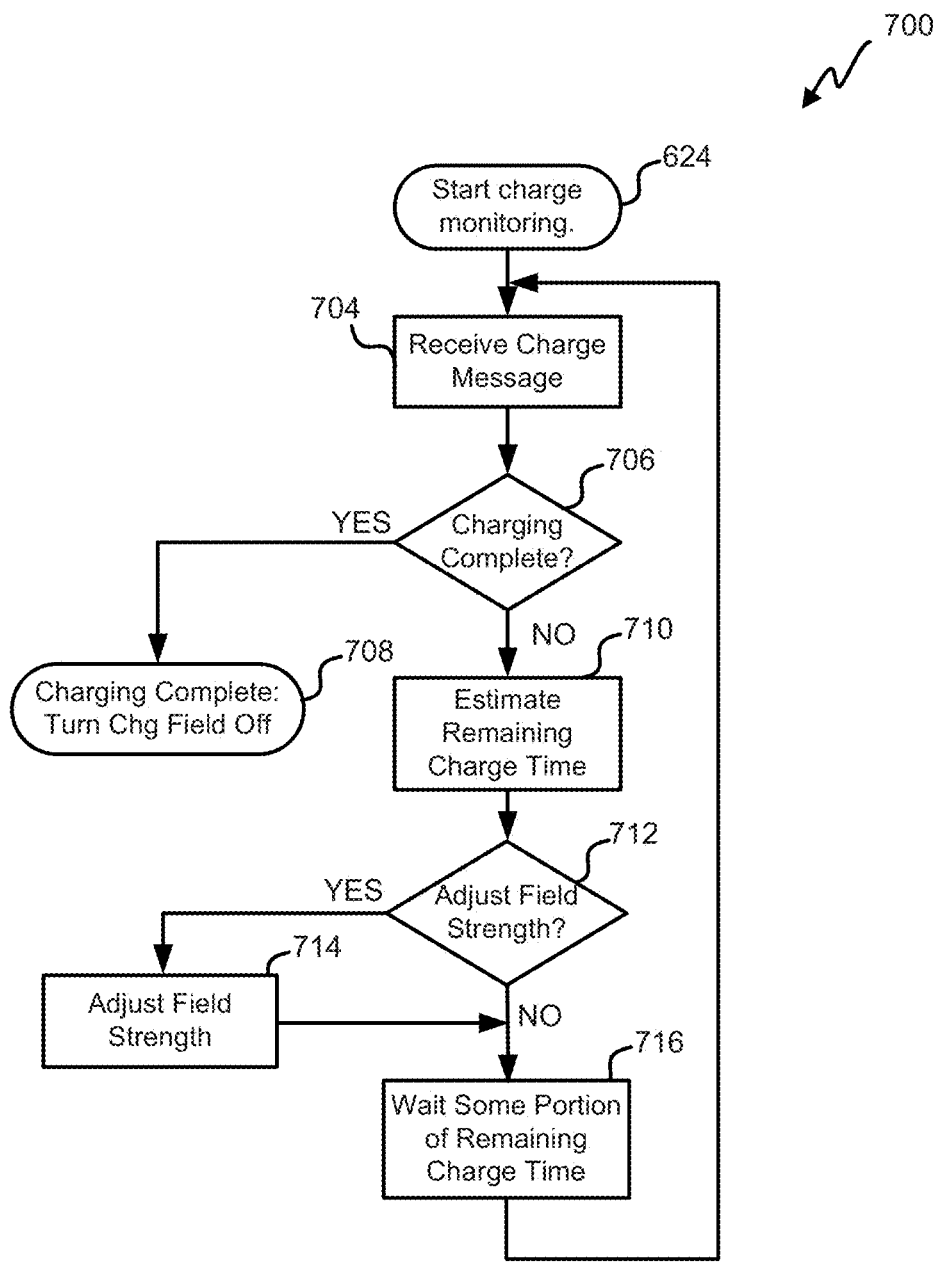
FIG. 7 is a flowchart illustrating one embodiment of a process for charge monitoring.

With reference now to FIG. 7, a flowchart illustrating one embodiment of a process 700 for charge monitoring is shown. In some embodiments, the process 700 can be performed to monitor and/or to control the charging. In some embodiments, this can result in improved charging efficiency and decreased risk of injury and/or discomfort created by the charging of the pulse generator 102, 104.

The process 700 continues from block 624 of FIG. 6 and proceeds to block 704, wherein the charge message is received. In some embodiments, the charge message can be received in response to a request send by the charger 116, and in some embodiments, the charge message can be received by the operation of pulse generator 102, 104 according to one or several stored protocols. In some embodiments, the charge message can include one or both of the communication indicating completed charging or communication requesting an adjustment in the charge strength. In some embodiments, and as discussed with respect to block 520 and 524 of FIG. 5, these messages can include one or both of a command or request for the charger 116 to take an action, and/or data that can be used by the charger 116 to determine whether to take an action such as, for example, stopping charging and/or adjusting the charge field strength. The charge message can be received by the network interface 400 of the charger 116.

After the charge message has been received, the process 700 proceeds to decision state 706, wherein it is determined if charging is complete. In some embodiments, this determination can include determining whether the charge message included a command/request to stop charging and/or whether the charge message included data indicative of completeness of charging. In some embodiments, the completeness of charging based on data received in the charge message can be determined by comparing the received data to one or several thresholds in the same manner as outlined in process 500 of FIG. 5.

If it is determined that charging is complete, then the process 700 proceeds to block 708 wherein the charge field is turned off. In some embodiments, this can include storing data relating to the completed charging such as, for example, the identification of the charged pulse generator, the amount of charge provided to the pulse generator, the internal resistance of the energy storage device of the pulse generator 102, 104, the duration of the charging event, or the like. In some embodiments, this information can be used to estimate the life of the pulse generator 102, 104 and/or the energy storage device 308 of the pulse generator 102, 104. This data can be stored in the memory of the charger 116 and/or transmitted to one or both of the clinician programmer 118 and the patient remote 120.

Returning again to decision state 706, if it is determined that charging is not complete, the remaining charge time can be estimated as indicated in block 710. In some embodiments, this estimate can be based on previous data collected relating to the charging of one or several pulse generators 102, 104, based on data received in the charge message including, for example, the charge state of the energy storage device 308, or the like. In some embodiments, this estimate can be generated by the charger 116 and/or received from the pulse generator 102, 104 as part of the charge message.

After the remaining charge time has been estimated, the process 700 proceeds to decision state 712 wherein it is determined whether to adjust the charge field strength. This determination can be based on the charge message, including information in the charge message and/or on the estimated remaining charge time. In some embodiments, this decision can include identifying whether the charge message included a command or request to adjust the strength of the charge field and/or determining whether information contained in charge message correlates with criteria for adjusting the strength of the charge message. In some embodiments, the correlation between information contained in the charge message and adjusting the strength of the charge message can be determined according to steps outlined with respect to process 500, and specifically according to block 516 and decision state 522, which steps can be performed, in some embodiments, by the charger 116.

If it is determined that the charge field strength should be adjusted, then the process 700 proceeds to block 714 wherein the field strength is adjusted. In some embodiments the adjustment of the charge field strength can include storing data relating to the adjustment and/or the circumstances leading to the adjustment. In some embodiments, this data can include the amount of charge provided until the adjustment, the amount of charge time until the adjustment, or the like. In some embodiments, this information can be used to estimate the life of the pulse generator 102, 104 and/or the energy storage device 308 of the pulse generator 102, 104. This data can be stored in the memory of the charger 116 and/or transmitted to one or both of the clinician programmer 118 and the patient remote 120.

After the charge field strength has been adjusted, or returning again to decision state 712, if it is determined that no adjustment to the charge field strength is needed, then the process 700 proceeds to block 716 and waits until a predetermined amount of time has passed. In some embodiments, the predetermined time can comprise a percent of the estimated remaining charge time. Advantageously, by waiting a percent of the estimated remaining charge time, the likelihood of overcharging is decreased. In some embodiments, the predetermined time can comprise, for example, 25 percent of the estimated remaining charge time, 50 percent of the estimated remaining charge time, 75 percent of the estimated remaining charge time, 80 percent of the estimated remaining charge time, 90 percent of the estimated remaining charge time, 95 percent of the estimated remaining charge time, 98 percent of the estimated remaining charge time, 99 percent of the estimated remaining charge time, and/or any other or intermediate percent of the remaining charge time. In some embodiments, this predetermined amount of time can be calculated by determining an estimated amount of time for the pulse generator 102, 104 to reach a predetermined charge state that is a percent of a fully charged charge state. In some embodiments, this percent can be a 70 percent charge state, an 80 percent charge state, a 90 percent charge state, a 95 percent charge state, a 98 percent charge state, a 99 percent charge state, and/or any other or intermediate percent charge state. After the process 700 has waited for the predetermined amount of time, the process 700 returns to block 704 and proceeds as outlined above.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of charging an energy storage device of an implantable pulse generator using an external charger, the method comprising:
   wirelessly receiving at the external charger an identifier corresponding to the implantable pulse generator;
   wirelessly receiving at the external charger information from the implantable pulse generator corresponding to a first sensed electrical field strength;
   at the external charger, changing the strength of the electrical field;
   after changing the strength of the electrical field, wirelessly receiving at the external charger information from the implantable pulse generator corresponding to a second sensed electrical field strength;
   in response to the received information corresponding to the first and second sensed electrical fields, determining not to recharge the first implantable pulse generator based on the information corresponding to the first sensed electrical field;
   selecting a second implantable pulse generator based on a first sensed electrical field strength at the second implantable pulse generator and a second sensed electrical field strength at the second implantable pulse generator; and
   charging the second implantable pulse generator, wherein charging the second implantable pulse generator comprises changing the strength of the electrical field so that the electrical field is detectable by the second implantable pulse generator and is not detectable by the first implantable pulse generator.

2. The method of claim 1, further comprising setting a first strength of the electrical field at the external charger.

3. The method of claim 2, wherein the first strength of the electrical field set at the external charger is zero.

4. The method of claim 1, wherein charging the energy storage device of the second implantable pulse generator further comprises changing the strength of the electrical field to a third strength at the external charger.

5. The method of claim 4, further comprising determining the third strength of the electrical field.

6. The method of claim 5, wherein the third strength of the electrical field is determined based on at least one of: a parameter of the implantable pulse generator, the external charger information corresponding to a first sensed electrical field strength, and the external charger information corresponding to the second sensed electrical field strength.

7. The method of claim 6, wherein the third strength of the electrical field is determined based on at least one of: a parameter of the implantable pulse generator, wherein the parameter of the implantable pulse generator identifies one of:
   a charge state of the energy storage device;
   a temperature;
   a shunt current; and
   a maximum charge rate of the energy storage device.

8. The method of claim 5, further comprising terminating charging when a desired charge state is achieved.

9. The method of claim 8 wherein the desired charge state is determined from one of a temperature and a shunt current.

10. A method of charging an energy storage device of an implantable pulse generator using an external charger, the method comprising:
    wirelessly receiving at the external charger an identifier corresponding to a first implantable pulse generator;
    wirelessly receiving at the external charger information from the first implantable pulse generator corresponding to a first sensed electrical field strength;
    at the external charger, changing the strength of the electrical field;
    after changing the strength of the electrical field, wirelessly receiving at the external charger information from the first implantable pulse generator corresponding to a second sensed electrical field strength; and in response to the received information corresponding to the first and second sensed electrical fields, determining not to recharge the first implantable pulse generators wherein determining not to recharge the first implantable pulse generator comprises: comparing the information corresponding to the second sensed electrical field to a threshold; and determining that the sensed electrical field is too weak to recharge the first implantable pulse generator;

selecting a second implantable pulse generator based on a first sensed electrical field strength at the second implantable pulse generator and a second sensed electrical field strength at the second implantable pulse generator; and charging the second implantable pulse generator, wherein charging the second implantable pulse generator comprises changing the strength of the electrical field so that the electrical field is detectable by the second implantable pulse generator and is not detectable by the first implantable pulse generator.

11. The method of claim 10, wherein the inability to recharge the first implantable pulse generator is determined if the information corresponding to the first sensed electrical field indicates a source of the electrical field other than the external charger.

* * * * *